(12) United States Patent
Barenholz et al.

(10) Patent No.: US 7,056,653 B2
(45) Date of Patent: Jun. 6, 2006

(54) DETECTION OF BINDING OF CHARGED SPECIES USING PH- OR POTENTIAL-SENSITIVE PROBES

(75) Inventors: Yechezkel Barenholz, Jerusalem (IL); Danielle Hirsch-Lerner, Jerusalem (IL); Rivka Cohen, Jerusalem (IL); Arie Dagan, Jerusalem (IL); Shimon Gatt, Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 09/780,757

(22) Filed: Feb. 8, 2001

(65) Prior Publication Data
US 2002/0012923 A1 Jan. 31, 2002

Related U.S. Application Data

(60) Provisional application No. 60/181,693, filed on Feb. 10, 2000.

(51) Int. Cl.
*C12Q 1/68* (2006.01)
*A01N 43/16* (2006.01)
(52) U.S. Cl. .............................. 435/4; 435/6; 424/1.21; 514/457; 549/283
(58) Field of Classification Search .................... 435/6; 514/457; 549/283; 424/1.21
See application file for complete search history.

(56) References Cited

U.S. PATENT DOCUMENTS 5,830,912 A * 11/1998 Gee et al. ................... 514/457

FOREIGN PATENT DOCUMENTS

WO WO 9711067 3/1997

OTHER PUBLICATIONS

Zuidam et al, "Electrostatic and structural properties of complexes involving plasmid DNA and cationic lipids commonly used for gene delivery", Biochim. Biophys. Acta (1998) 1368:115-128.*
Nicholaas Jan Zuidam and Yechezkel Barenholz, Characterization of DNA-lipd complexes commonly used for gene delivery:, International Journal of Pharmaceutics, vol. 183, pp. 43-46, 1999.
Chatelut, M., et al., "Natural ceramide is unable to escape the lysosome, in contrast to a fluorescent analogue" *FEBS Letters 426*:102-106 (1998).
Ferrari, M.E., et al., Analytical Methods for the Characterization of Cationic Lipid-Nucleic Acid Complexes *Human Gene Therapy 9*:341-651 (1998).
Fromherz, P., "Lipid Coumarin Dye as a Probe of Interfacial Electrical Potential in Biomembranes" *Methods in Enzymology 171*:376-387 (1989).
Giudici, M.L., et al., "Uptake and metabolism of fluorescent ceramide analogs by rat oligodendrocytes in culture" *FEBS 314* (3) :471-476 (1992).
Kraayenhof, R., et al., "Probing Biomembrane Interfacial Potential and pH Profiles with a New Type of Float-like Fluorophores Positioned at Varying Distance from the Membrane Surface" *Biochemistry 32*:10057-10066 (1993).
Kraayenhof, R., et al., "Monovalent cations differentially affect membrane surface properties and membrane curvature, as revealed by fluorescent probes and dynamic light scattering" *Biochimica et Biophysica Acta 1282*:293-302 (1996).
Marchesini, S., et al., "A novel fluorescent pH indicator for the acidic range" *Biochemistry International 27* (3):545-550 (1992).
Pal, R., et al., "Characterization of the Fluorophore 4-Heptadecyl-7-hydroxycoumarin: A Probe for the Head-Group Region of Lipid Bilayers and Biological Membranes" *Biochemistry 24*:573-581 (1985).
Zelphati, O., et al., "Effect of serum components on the physico-chemical properties of cationic lipid/oligonucleotide complexes and on their interactions with cells" *Biochimica et Biophysica Acta 1390*:119-133 (1998).
WU, et al., "Hydration and stability of sulfatide-containing phosphatidylethanolamine small unilamellar vesicles," *Biochimica et Biophysica Acta 1416*:285-294 (1999).
Nichols, "Kinetics of fluorescent-labeled phosphatidylcholine transfer between nonspecific lipid transfer protein and phospholipid vesicles," *Biochemistry 27*:1889-1896 (1988).

* cited by examiner

*Primary Examiner*—Jeffrey Fredman
(74) *Attorney, Agent, or Firm*—Browdy and Neimark, PLLC

(57) ABSTRACT

The extent of binding of a moiety, such as a biomolecule, to a surface, where the local environment at the surface has a pH or surface potential which is altered upon binding of the moiety, is determined by stably incorporating at the surface a probe which contains a pH- or potential-sensitive fluorophore.

21 Claims, 13 Drawing Sheets

DETECTION OF BINDING OF CHARGED SPECIES USING PH- OR POTENTIAL-SENSITIVE PROBES

This application claims priority to U.S. provisional application No. 60/181,693, filed Feb. 10, 2000, which is hereby incorporated by reference in its entirety.

FIELD OF THE INVENTION

The present invention relates to methods and compositions for determining the extent of binding of a moiety, such as a biomolecule, to a surface, or dissociation of the moiety from the surface, where the local environment at the surface has a pH or surface potential which is altered upon binding of the moiety.

BACKGROUND OF THE INVENTION

Many reactions of significance in biological systems, whether in living systems or in the laboratory, involve electrostatic interactions of charged species at a surface. For example, the use of cationic liposomes for the delivery of DNA into cells has been the subject of extensive study. The cationic carriers interact with the negatively charged DNA to form DNA-lipid complexes, which are believed to enter cells primarily by adsorptive endocytosis.

Fluorescently labeled probes have been used to study binding of DNA to cationic liposomes, as described, for example, in Zelphati et al., *Biochim Biophys Acta* 1390(2): 119–33 (1998). In this study, detection relied on a fluorescence quenching, which required that the molecule being detected (DNA) also be labeled, and that it be in close enough proximity to the probe to allow quenching. Zelphati also reported that background fluorescence from serum interfered with the measurements. Probes containing the pH-dependent fluorescent molecule 7-hydroxycoumarin have been used to study changes in electric potential at surfaces (Barenholz and Zuidam, *Int J Pharm* 183(1):43–6, June 1999). However, the use of such methods in studying lipid bilayers, especially in biological systems, is hampered by the instability of the probe in the bilayer.

Accordingly, there is a need for improved methods of observing such interactions, in a stable and reproducible manner.

SUMMARY OF THE INVENTION

The present invention includes, in one aspect, a method for determining binding of a species at a surface having a local environment at a given pH or surface potential, where the binding is effective to alter the pH or potential. In accordance with the method, a probe which comprises a pH- or potential-sensitive fluorophore is stably incorporated at the surface, and a change in a fluorescent property of the fluorophore is observed upon binding (or dissociation) of the species at the surface, due to a change in surface potential or pH. The method thus detects changes in the environment of the probe, not necessarily dependent on interactions of the probe with a specific molecule. Both specific and non-specific interactions at the surface can be detected.

In one embodiment, where the surface is the surface of a lipid bilayer, such as a lipid vesicle or cell membrane, the probe comprises a pH- or potential-sensitive fluorophore attached to a steroid or to a lipid having at least two alkyl or alkenyl chains at least 14 carbon atoms in length. The steroid or lipid serves to stably incorporate the probe within the lipid bilayer.

In one embodiment, the binding species is a biomolecule having groups which are positively or negatively charged at a selected pH between about 2.0 and 12.0, preferably between about 4.0 and 9.0, and more preferably between about 4.5 and 7.5. Such biomolecules include nucleic acids and proteins comprising amino acids with acidic or basic side groups. The surface may also comprise groups which are positively or negatively charged at a selected pH between about 2.0 and 12.0, preferably between about 4.0 and 9.0, and more preferably between about 4.5 and 7.5. Such surfaces include lipid bilayers comprising one or more lipids having a cationic head group, such as a quaternary ammonium group. Binding of the species to the surface may be electrostatic in nature. It may also be receptor-ligand based, where one of the species and the surface comprises a ligand, and the other comprises a receptor for the ligand.

Fluorophores which may be employed in the probe include pH-sensitive lissamine rhodamine, 7-hydroxycoumarin, fluorescein, and pH- or potential-sensitive derivatives thereof. Preferably, upon incorporation of the probe into or at the surface, the fluorophore is separated from the surface by a distance equal to or less than about 15 nm.

In another embodiment, the method employs a polymer to which the fluorophore is stably bound, e.g. via a covalent linkage. In this case, the method comprises observing a change in a fluorescent property of the fluorophore upon binding (or dissociation) of a species at the surface of the polymer, due to a change in surface potential or pH. Such polymers may be in various forms such as micro- or nano-particles, or as sheets; e.g. cellulose-based polymers.

The invention also provides a probe consisting of 7-hydroxycoumarin conjugated, at the 3-, 4-, 5-, 6- or 8-position, to a lipid having at least two alkyl or alkenyl chains at least 14 carbon atoms in length, where the lipid is preferably a dialkyl or dialkenyl phosphatidyl ethanolamine. In one embodiment, the probe consists of 7-hydroxycoumarin conjugated via a 3-carboxamide linkage to the head group nitrogen of a dialkyl or dialkenyl phosphatidyl ethanolamine, such as described in Example 2.

These and other objects and features of the invention will become more fully apparent when the following detailed description of the invention is read in conjunction with the accompanying drawings.

DETAILED DESCRIPTION OF THE INVENTION

I. Definitions

Figure 1:
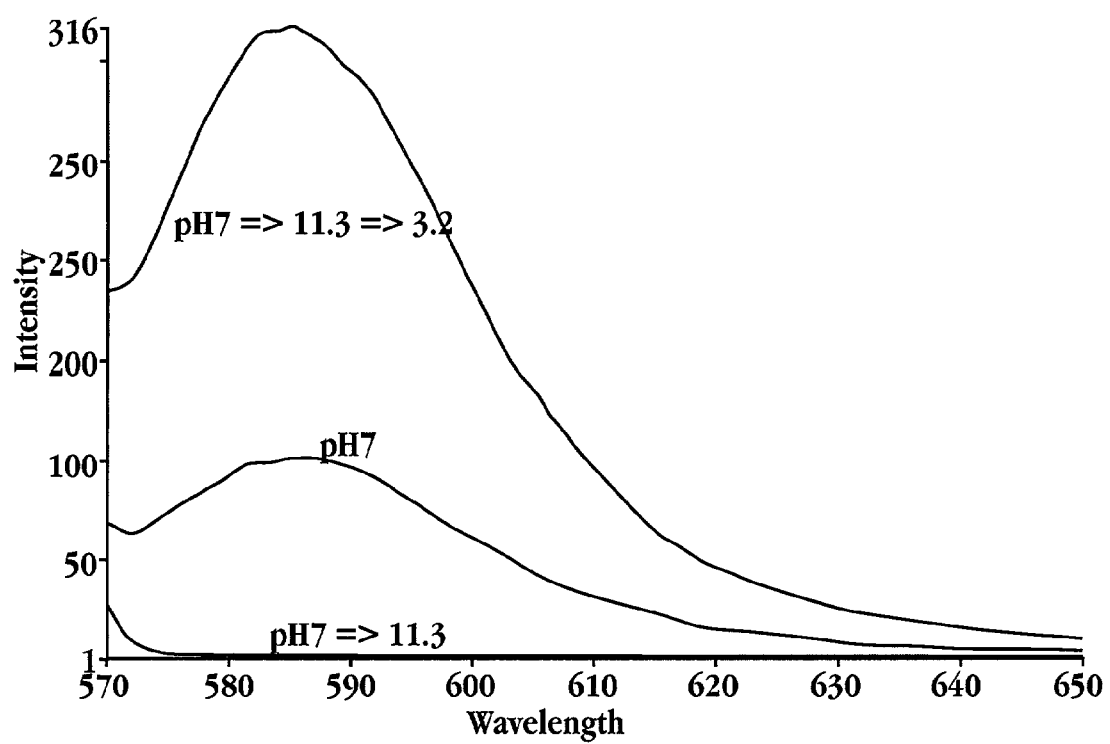
FIG. 1 shows fluorescence spectra of pH-sensitive lissamine rhodamine-dioleoyl phosphatidyl ethanolamine (LR-PE)

The terms below have the following meanings unless indicated otherwise.

A "pH sensitive" lissamine rhodamine is a 2'sulfonamide substituted lissamine rhodamine. An example is lissamine rhodamine 2'-N-methyl sulfonamide, whose structure is shown below, where R=methyl (see S. Marchesini et al., *Biochem. International* 27(3):545–50, July 1992). Such compounds undergo a pH-dependent conversion to a spiro-isothiazoline structure, as described in Marchesini et al. The isomeric 4'-sulfonamide-2'-sulfonic acid does not exhibit such behavior.

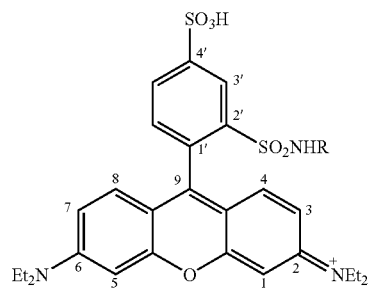

The 2' sulfonamide may be differently substituted, as long as the nitrogen of the sulfonamide group bears a hydrogen atom. The R group could be, for example, alkyl, aryl, aralkyl, or a lipid moiety. For example, a lipid such as a phosphatidyl ethanolamine may be conjugated at this position via the ethanolamine moiety, in preparing a pH-sensitive probe, such as the probe designated herein as "pH-sensitive lissamine rhodamine-dioleoyl phosphatidyl ethanolamine" (pH-sensitive LR-PE or LR-DOPE).

Derivatives of pH-sensitive LR compounds further include molecules having one or more additional substituents, preferably selected from the group consisting of halogen, alkyl, alkoxy, hydroxy, amino, alkylamino, carboxylic acid or ester, carboxylic amide, or sulfonic acid or ester, such that the pH- or potential-sensitive fluorescent properties of the molecule are not substantially affected. Examples of such derivatives include compounds in which one or more substituents selected from lower alkyl, amine, lower alkylamine, carboxyl, hydroxyl, and halogen is attached directly to one or more of the rings. The substituents on the existing 2,6-amine groups may be selected from hydrogen and lower alkyl (i.e. $C_1$ to $C_4$ alkyl, branched or unbranched). However, as noted above, the nitrogen of the sulfonamide group must bear at least one hydrogen atom.

"Vesicle-forming lipids" refers to amphipathic lipids which have hydrophobic and polar head group moieties, and which (a) can form spontaneously into bilayer vesicles in water, as exemplified by phospholipids, or (b) are stably incorporated into lipid bilayers, with the hydrophobic moiety in contact with the interior, hydrophobic region of the bilayer membrane, and the polar head group moiety oriented toward the exterior, polar surface of the membrane.

The vesicle-forming lipids of this type typically include one or two hydrophobic acyl hydrocarbon chains or a steroid group and may contain a chemically reactive group, such as an amine, acid, ester, aldehyde or alcohol, at the polar head group. Included in this class are the phospholipids, such as phosphatidyl choline (PC), phosphatidyl ethanolamine (PE), phosphatidic acid (PA), phosphatidyl inositol (PI), and sphingomyelin (SM), where the two hydrocarbon chains are typically between about 14–22 carbon atoms in length, and have varying degrees of unsaturation. Other vesicle-forming lipids include glycolipids, such as cerebrosides and gangliosides, and sterols, such as cholesterol.

"Cationic lipids" include lipids having cationic polar head groups, typically containing a quaternary ammonium group. These lipids can have a variety of chain lengths and unsaturation in the acyl groups. Such lipids are commonly used in nucleic acid transfection; examples include DOTMA (N-(1-(2,3-dioleoyloxy)propyl)-N,N,N-triethylammonium) and DOTAP (1,2-dioleoyl-3-trimethylammonium propane). The TAP and TMA lipids (and the cationic lipids DOSPA, N-[2-[[2,5-bis[(3-aminopropyl)amino]-1-oxopentyl]amino]
ethyl]-N,N-dimethyl-2,3-bis[(1-oxo-9-octadecenyl)oxy]-1-
propanaminium, and DMRIE, N-(2-hydroxyethyl)-N,N-
dimethyl-2,3-bis(tetradecyloxy)-1-propanaminium) have a
fixed charge on the ammonium group, while the DAP series
(1,2-diacyl 3-trimethylammonium propane) have a titratable
hydrogen ion on the polar group. These lipids carry a neutral
charge at physiological pH (about 6.8 to 7.4) but carry a net
positive charge in the lower pH environment of an endosome
(about 4.5 to 6.5).

"Alkyl" refers to a fully saturated acyclic monovalent
radical containing carbon and hydrogen, which may be
branched or a straight chain. Examples of alkyl groups
include methyl, ethyl, isopropyl, t-butyl, n-heptyl, n-decyl,
and n-octadecyl. "Alkenyl" refers to an unsaturated acyclic
monovalent radical containing carbon and hydrogen, which
may be branched or a straight chain. The alkenyl group may
be monounsaturated or polyunsaturated.

"Aryl" refers to a substituted or unsubstituted monovalent
aromatic radical having a single ring (e.g., benzene) or two
condensed rings (e.g., naphthyl). This term includes het-
eroaryl groups, which are aromatic ring groups having one
or more nitrogen, oxygen, or sulfur atoms in the ring, such
as furyl, pyrrole, pyridyl, and indole. By "substituted" is
meant that one or more ring hydrogens in the aryl group is
replaced with a halide such as fluorine, chlorine, or bromine;
with a lower alkyl group containing one or two carbon
atoms; nitro, amino, methylamino, dimethylamino, meth-
oxy, halomethoxy, halomethyl, or haloethyl.

"Aralkyl" refers to an alkyl, preferably lower alkyl,
substituent which is further substituted with an aryl group;
one example is a benzyl group.

The term "nucleic acid" or "polynucleotide" includes
naturally occurring DNA and RNA as well as synthetic
oligonucleotide analogs which comprise some level of
charged intersubunit linkages; e.g. phosphate or phospho-
rothioate linkages.

"Amino acids with acidic or basic side groups" include
aspartic acid, glutamic acid, lysine, arginine, and histidine,
the side groups of which carry a positive or negative charge
at a selected pH between about 4.5 and 7.5.

"Stably incorporated", with respect to a probe incorpo-
rated in a lipid bilayer, indicates that the probe has a low
desorption rate from the bilayer. This can be accomplished
by employing an anchoring hydrophobic group such as a
steroid or a dialkyl or dialkenyl lipid having carbon chains
14 carbons or greater in length.

Abbreviations:
AM-TIS-FITC: FITC-S-d-5'(GGG AAG GAT GGC GCA CGC TG)
Bcl2-TIAS-FITC: FITC-S-d-5'(CAG CGT GCG CCA TCC TTC CC)
DOPC: dioleoyl phosphatidyl choline
PE: a dialkyl or dialkenyl phosphatidyl ethanolamine
DOPE: dioleoyl phosphatidyl ethanolamine
DPPE: dipalmitoyl phosphatidyl ethanolamine
POPC: palmitoyloleoyl phosphatidyl choline
POPG: palmitoyloleoyl phosphatidyl glycerol
DOTAP: 1,2-dioleoyl-3-trimethylammonium propane
DOSPA: N-[2-[[2,5-bis[(3-aminopropyl)amino]-1-oxo-pentyl]amino]ethyl]-N,N-dimethyl-2,3-bis[(1-oxo-9-octadecenyl)oxy]-1-propanaminium
DMRIE: N-(2-hydroxyethyl)-N,N-dimethyl-2,3-bis(tet-radecyloxy)-1-propanaminium
Chol: cholesterol Liposomal compositions described using the names of
two components include equal molar amounts of each
component; for example, DOTAP:DOPE refers to
50:50 DOTAP:DOPE.

II. pH- or Potential-sensitive Fluorescent Probes for Detec-
tion of Binding

According to the present invention, a change in local pH
or surface potential at a surface upon binding of a species,
such as a biomolecule, is observed via a pH- or potential-
sensitive fluorophore associated with the surface. In one
embodiment, the biomolecule is a polynucleotide. Binding
is typically electrostatic in nature; however, it may also be
receptor-ligand based, rather than strictly electrostatic, as
long as the binding alters the pH or potential of the surface
containing the probe.

A fluorophore that is "pH- or potential-sensitive", in
general, is one having one or more fluorescent properties
which undergoes an observable change upon a change in
environment electrical potential and/or pH. Such properties
may include fluorescent intensity (I), ratio of fluorescent
intensities at different excitation or emission wavelengths,
fluorescent life time, steady state or time dependent fluo-
rescence polarization, etc. Preferably, the property observed
is based on fluorescent intensity. Such pH- or potential-
sensitive fluorophores include fluorescein, 7-hydroxycou-
marin, and pH-sensitive lissamine rhodamine, as defined
above.

The surface may be, for example, the surface of a lipid
vesicle (liposome), particularly a lipid vesicle comprising
lipids having cationic head groups, such as are commonly
used for DNA transfection. Alternatively, the surface may be
a cell membrane. A lipid conjugated with a pH- or potential-
sensitive fluorophore is incorporated into the liposome or
other membrane bilayer; the level of incorporation is typi-
cally about 0.2 to 0.5 mole percent. The probes may also be
incorporated into lipid monolayer structures, such as stable
micelles and emulsion droplets, as well as other lipid phases,
such as the cubic phase.

A. Preparation of Probes

In one embodiment, the probe comprises a pH- or poten-
tial-sensitive fluorophore attached to a steroid or to a lipid
having at least two alkyl or alkenyl chains at least 14 carbon
atoms in length. The steroid or lipid, such as a phospholipid
or sphingolipid, may be conjugated to the fluorophore by
known synthetic methods. Positively charged, negatively
charged, and neutral (zwitterionic) lipids may be used. For
example, a nucleophilic functionality on a steroid or on the
polar head group of a phospholipid or sphingolipid, such as
a hydroxyl or amino group, may be reacted with a carboxyl
or sulfonyl moiety on the fluorophore. DOSPA-type lipids,
having a polyamine head group, and phosphatidyl ethano-
lamines, bearing a primary amino group, are particularly
useful for this purpose. When the fluorophore is attached via
a polyamine moiety, the probe may include more than one
fluorophore, or a cationic probe may result, depending on
how many amine groups are derivatized with the fluoro-
phore.

Fluorescein derivatives of PE's having various alkyl chain
lengths are commercially available (Avanti Polar Lipids,
Alabaster, Ala.). Commercially available lissamine
rhodamine, e.g. Lissamine Rhodamine B chloride, available
from Molecular Probes (Eugene, Oreg.), is a mixture of two
isomers, the 2'-sulfonyl chloride-4'-sulfonic acid (using the
numbering scheme shown above) and the reverse isomer.
The former, when reacted with a primary amine to form a
2'-sulfonamide, forms a pH-sensitive compound. The latter forms a 4'sulfonamide, which is not pH-sensitive. Accordingly, pH-sensitive probes are prepared by conjugating a lipid bearing a primary amine, such as PE, to the 2'-sulfonyl chloride of the 2'-sulfonyl chloride4'-sulfonic acid isomer. The isomers of the commercial preparation may be separated either before or after conjugation. See Example 1, below.

Alternatively, the 2'-sulfonyl chloride may be reacted with, for example, an alkyl amine to form a pH-sensitive alkyl sulfonamide, such as lissamine rhodamine 2'-N-methyl sulfonamide, which can then be conjugated with a lipid at the 4' position.

Probes based on 7-hydroxycoumarin (7-HC) may be prepared by reacting a PE with a 7-HC derivative having a carboxyl or sulfonyl moiety at its 3, 4, 5, 6, or 8 position, preferably at the 3 or 4 position. Example 2, below, illustrates reaction of a PE with 7-hydroxycoumarin-3-carboxylic acid succinimidyl ester.

It is understood that a fluorophore may be conjugated to a lipid via various linkages in addition to those specifically described above, using conventional synthetic methods. Bifunctional or polyfunctional groups, such as diols or polyamines, e.g. spermine or spermidine, may be used as linking groups. For example, PEG (polyethylene glycol)-derivatized phospholipids, such as those employed in Stealth™ liposomes, are well known. Probes having a PEG chain linked to a phospholipid head group at one terminus and a fluorophore at the other terminus have been prepared by the authors, and were used to sense interaction of liposomes containing the probes with proteins, according to methods described below.

In another embodiment, the fluorophore is attached, preferably covalently, to a polymer. For example, FIGS. 12A–B, discussed further below, illustrate the pH dependent fluorescence of a an oligonucleotide-fluorescein conjugate and a dextran-fluorescein conjugate. The level of derivatization is typically between about 0.1 and 5.0 weight percent fluorophore:polymer, preferably between about 0.3 and 3.0 weight percent. Preferred polymers include, for example, polysaccharide polymers, such as dextrans and cellulose-based polymers, polyacrylates and polymethacylrates, polyesters, polyethers, polyamines, polyamides, polyimides, polystyrenes, polyamino acids, such as polylysine or polyarginine, and fluoropolymers. Such polymers may be in various forms such as micro- or nanoparticles, fibers, or sheets.

B. Effect of pH on Probes

A probe consisting of pH-sensitive lissamine rhodamine linked, via a 2'sulfonamide, to dioleoyl phosphatidyl ethanolamine (pH-sensitive LR-PE, 1) was prepared as described in Example 1. As an illustration of the pH dependence of the probe, the fluorescence at 585 nm was observed in aqueous preparations having a range of different pH values, as shown in FIG. 1. The effect was shown to be reversible by observing the fluorescence of 1 at 585 nm as the pH of a single preparation was changed in sequence from 7.0 to 11.3 to 3.2.

C. Effect of pH on Liposomes Incomorating Probes

Figure 2:
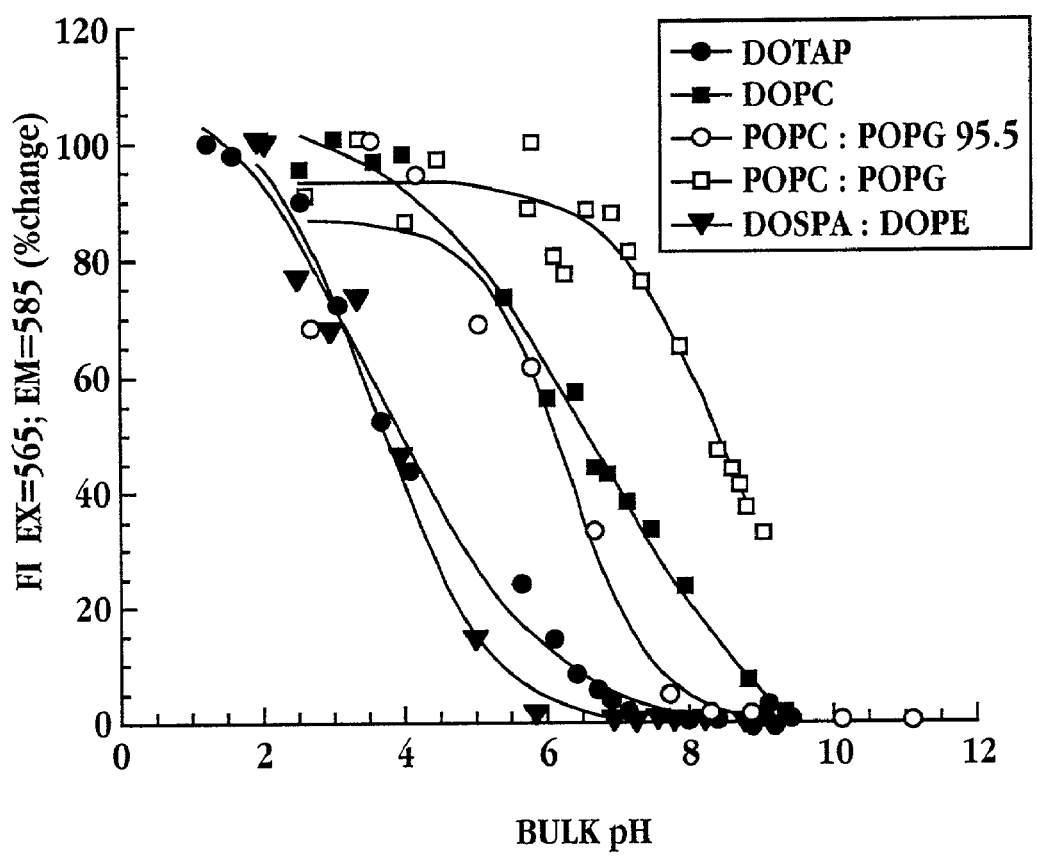
FIG. 2 shows the change in 585 nm fluorescence with increasing pH of aqueous preparations of LUV composed of DOTAP, DOPC, 95:5 POPC:POPG, POPC:POPG, and DOSPA:DOPE, respectively, each containing 0.2 mole % pH-sensitive LR-PE.

The effect of change in pH on liposomes containing pH-sensitive LR-PE is shown in FIG. 2. Aqueous suspensions of LUV (large unilamellar vesicles) composed of, respectively, DOTAP, DOPC, 95:5 POPC:POPG, POPC:POPG, and DOSPA:DOPE, each containing 0.2 mole % pH-sensitive LR-PE, were prepared as described in Example 3. This level of probe was employed in all experiments described herein, unless indicated otherwise. The fluorescence of these compositions was observed with increasing pH. As shown in the Figure, fluorescence decreased significantly as pH increased and was essentially absent for most of these compositions at pH 8 and above.

Such titration curves can be used as calibration curves, and to determine the apparent pKa of the probe moiety, from which surface pH and surface potential can be determined. Differing pKa's were observed for liposomes composed of cationic (DOTAP, DOSPA), neutral (PC's and PE's) and anionic (POPG) lipids, as is clear from FIG. 2. A similar pH-dependent effect was observed for DOTAP/Chol liposomes containing the probe, in which case the apparent pKa was about 3.25.

For DOTAP/DOPE liposomes containing a similar quantity of commercially available LR-PE, which is non pH sensitive, no such effect was observed. Fluorescence emission intensity at 585 nm remained essentially unchanged over a pH range of 4.0 to 9.3 (data not shown).

Figure 3:
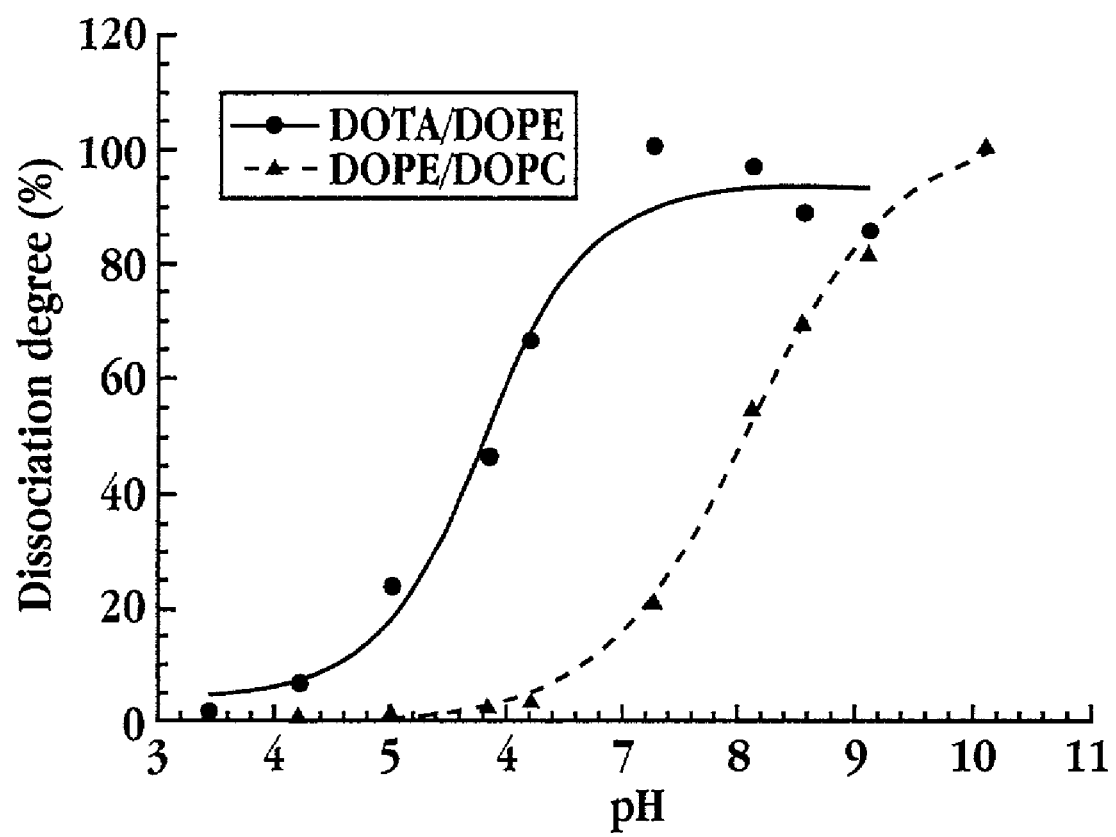
FIG. 3 shows the titration of DOPE/DOPC and DOPE/DOTAP liposomes, each containing 0.2 mole % of a probe consisting of fluorescein attached to the headgroup of phosphatidyl ethanolamine (F-PE)

FIG. 3 shows the titration of DOPE/DOPC and DOPE/DOTAP liposomes, each containing 0.2 mole % of a probe consisting of fluorescein attached to the headgroup of phosphatidyl ethanolamine (F-PE, available from Avanti Polar Lipids, Alabaster, Ala.). The figure shows the large difference in apparent pKa of the probe (about 2.3 pH units) between liposomes containing the neutral zwitterionic DOPC and the cationic lipid DOTAP. The direction of the shift is consistent with the cationic DOTAP/DOPE liposome surface.

Figure 4:
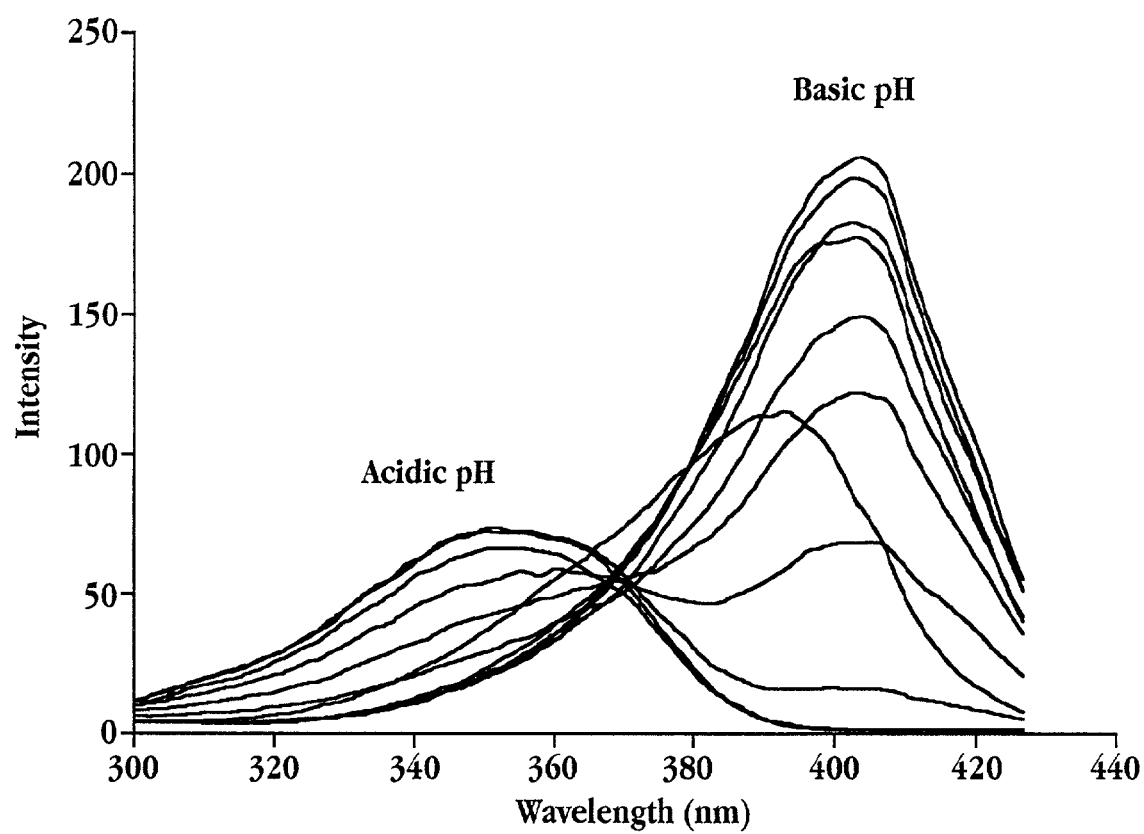
FIG. 4 shows fluorescence spectra (emission at 445 nm) of DOTAP liposomes (41.3 mM DOTAP containing 0.2 mole % 7-hydroxycoumarin dioleoyl phosphatidyl ethanolamine (HC-PE) at a series of different pH values.
Figure 5:
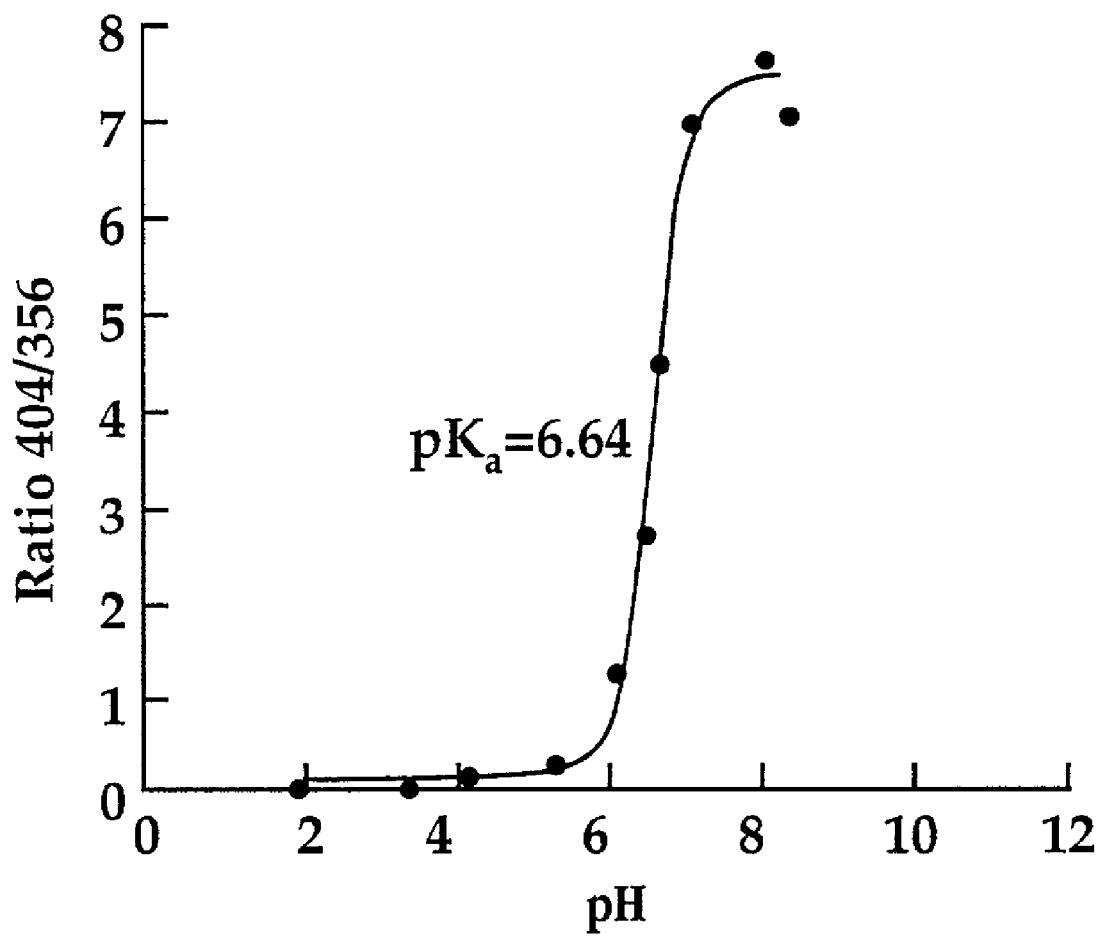
FIG. 5 is a titration curve for the DOTAP liposomes of FIG. 2, showing the ratio of fluorescence intensity at 404 nm to that at 356 nm (emission at 445 nm) with increasing pH.

FIGS. 4–5 show the similar effect of pH on fluorescence measurements of DOTAP liposomes (approx. 41.5 mM DOTAP) containing 0.2 mole % of a probe consisting of 7-hydroxycoumarin linked to dioleoyl phosphatidyl ethanolamine (HC-PE, prepared as described in Example 2).

To demonstrate the stability of probe incorporation in liposome bilayers, the lipid-fluorophore conjugate probe, HC-PE, was incorporated into DOTAP liposomes (HEPES buffer, pH 7.4), the fluorescence intensity ($F_0$) was recorded, and then a differently-charged (zwitterionic) lipid, DOPC, was added. The fluorescence intensity was followed with time (Ex=405 nm, Em=447 nm with a filter at 430 nm, slits 2.5/2.5). As the Table below shows (columns 1–3), little or no change in fluorescence was observed, indicating that little or none of the HC-PE migrated to the DOPC liposomes. A similar effect was observed for HC-PE incorporated into DOPE liposomes, with addition of DOTAP (columns 4–6).

With DOTAP/4-heptadecyl 7-hydroxycoumarin (HC-HD), in contrast, $F/F_0$ is reduced from 1 to 0.65 in 4 minutes on addition of DOPC (columns 7–9), indicating that the HC-HD, which has only one fatty alkyl chain, is not stably associated with the bilayer membrane, and equilibrates between liposomes of different composition.

TABLE 1

| DOTAP/HC-PE | Time (sec) | $F/F_0$ | DOPE/HC-PE | Time (sec) | $F/F_0$ | DOTAP/HC | Time (sec) | $F/F_0$ |
|---|---|---|---|---|---|---|---|---|
| + DOPC (0.2 mM) | 0 | 1.00 | + DOTAP (0.2 mM) | 0 | 1.00 | + DOPC (0.2 mM) | 0 | 1 |
| | 60 | 0.96 | | 60 | 1.00 | | 240 | 0.65 |
| | 180 | 0.96 | | 180 | 1.00 | | | |
| | 300 | 0.96 | | 300 | 0.99 | | | |

TABLE 1-continued

| DOTAP/<br>HC-PE | Time (sec) | $F/F_0$ | DOPE/<br>HC-PE | Time<br>(sec) | $F/F_0$ | DOTAP/<br>HC | Time<br>(sec) | $F/F_0$ |
|---|---|---|---|---|---|---|---|---|
| | 720 | 0.95 | | 420 | 0.99 | | | |
| | 900 | 0.95 | | 600 | 0.98 | | | |

Figure 6:
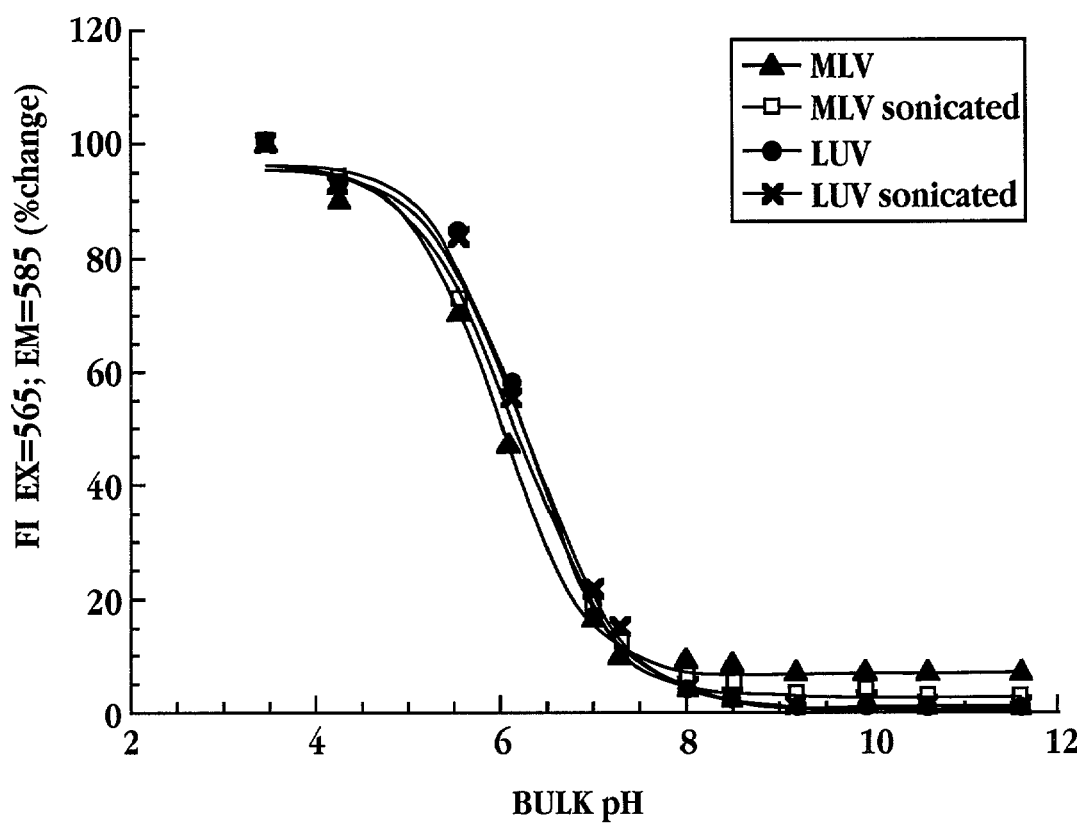
FIG. 6 shows the change in 585 nm fluorescence with increasing pH of aqueous preparations of LUV and MLV composed of 95:5 POPC:POPG containing 0.2 mole % pH-sensitive LR-PE, before and after sonication for 2 min at room temperature.

FIG. 6 further illustrates the stability of incorporation of the lipid-fluorophore probe within the liposomes. The pH-dependent fluorescence of MLV and LUV composed of 95:5 POPC:POPG and containing 0.2 mole % pH-sensitive LR-PE was observed as above, before and after sonication for 2 minutes at room temperature (Transsonic™ 460/H, 35 kHz, 285 watts, Elma Bergwies, Austria). As the figure shows, little or no probe was lost from the vesicles during sonication.

D. Effect of Binding of Charged Species to Liposomes

Figure 7:
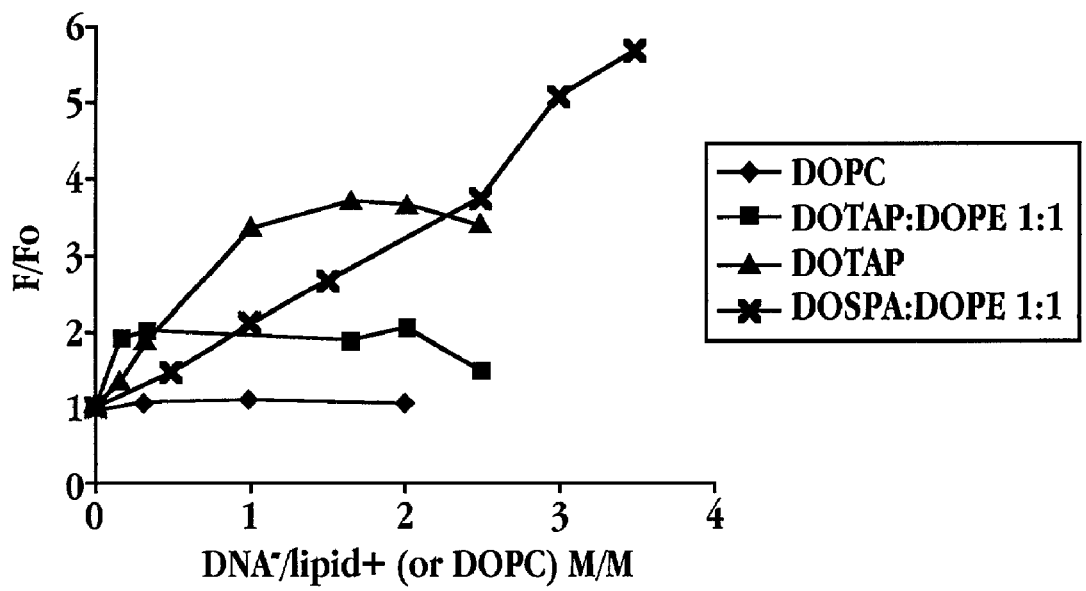
FIG. 7 shows the relative change in 585 nm fluorescence of aqueous preparations of LUV composed of DOTAP, DOPC, and DOTAP:DOPE, respectively, each containing 0.2 mole % pH-sensitive LR-PE, on addition of increasing amounts of hGH-CMV DNA plasmid (human growth hormone gene inserted into a 5.5 kbp plasmid driven by the early promoter and enhancer of cytomegalovirus)

The probes are particularly useful for detecting binding of charged species, such as polynucleotides, to a surface, such as the surface of a vesicle comprising cationic lipids. As shown in FIG. 7, for liposomes composed of the cationic transfection agent DOTAP, and containing 0.2 mole % pH-sensitive LR-PE, fluorescence increased significantly upon addition of increased levels of DNA, demonstrating binding of the DNA and consequent neutralization of the charges on the cationic head groups. For liposomes composed of 1:1 DOTAP: DOPE, a less pronounced change was observed. A similar result was seen for DOTAP:Chol liposomes, where $F/F_0$ was about 0.4 at a DNA/lipid ratio of 2.0. For liposomes composed of (neutral) DOPC, little or no change in fluorescence was observed, indicating that little or no DNA binding to the DOPC liposomes took place.

Figure 8:
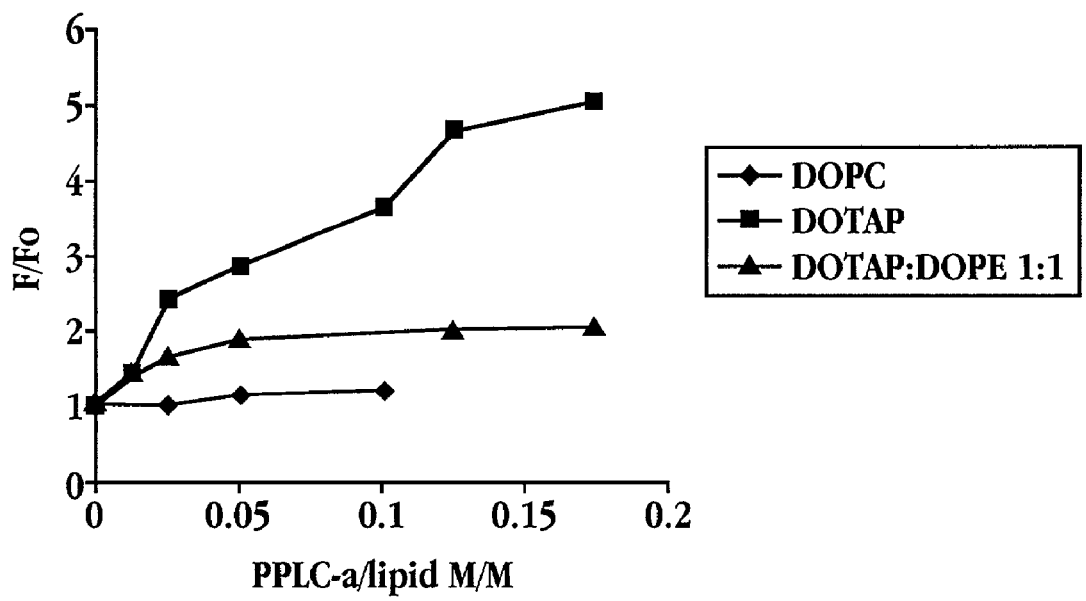
FIG. 8 shows the relative change in 585 nm fluorescence of aqueous preparations of LUV composed of DOTAP, DOPC, and DOTAP:DOPE, respectively, each containing 0.2 mole % pH-sensitive LR-PE, on addition of increasing amounts of PP2C-α (protein phosphatase 2C alpha)

Similar experiments were carried out with these liposomal compositions, adding the enzyme PP2C-α (protein phosphatase 2C alpha) in increasing amounts (FIG. 8). Again, the increase in fluorescence was significant for the DOTAP liposomes, moderate for the DOTAP:DOPE liposomes, and minimal for the DOPC liposomes.

Although pH-sensitive LR-PE probes are employed in the examples above, the method can be carried out using any group which can be linked to the fluorophore and is effective to anchor the probe molecule to or within the surface being observed. For use in lipid vesicles or bilayers, particularly in vivo, the hydrophobic molecule must be effective to anchor itself within the vesicle bilayer, leaving the fluorophore exposed at the surface. Such molecules include other vesicle-forming lipids, preferably dialkyl or dialkenyl phospholipids, as described above.

Binding of charged species to cationic liposomes was also determined using the probes HC-DOPE, prepared as described in Example 2, and fluorescein-labeled DPPE. The effect on fluorescence of binding of hGH-CMV DNA plasmid (human growth hormone gene inserted into a 5.5 kbp plasmid driven by the early promoter and enhancer of cytomegalovirus) to DOTAP liposomes containing 0.2 mole % HC-PE is shown in the Table below. DNA⁻/L⁺ represents the charge molar ratio.

TABLE 2

| DNA⁻/L⁺ | Intensity* | $F/F_0$ | Turbidity† |
|---|---|---|---|
| 0 | 120.11 | 1 | 34.67 |
| 0.5 | 88.9 | 0.74 | 516.41 |

TABLE 2-continued

| DNA⁻/L⁺ | Intensity* | $F/F_0$ | Turbidity† |
|---|---|---|---|
| 1 | 76.24 | 0.63 | 632.86 |
| 1.5 | 79.08 | 0.66 | 631.3 |

82.7 μM DOTAP/HC-PE in acetate buffer (pH 5.7)
Ex = 405 nm, Em = 447 nm; filter 430 nm (slits 2.5/2.5).
*Measurement was performed 5 mins after addition of DNA.
†Turbidity was measured as light scattering at 90° using a spectrophotometer at emission and excitation wavelength of 600 nm.

Figure 9:
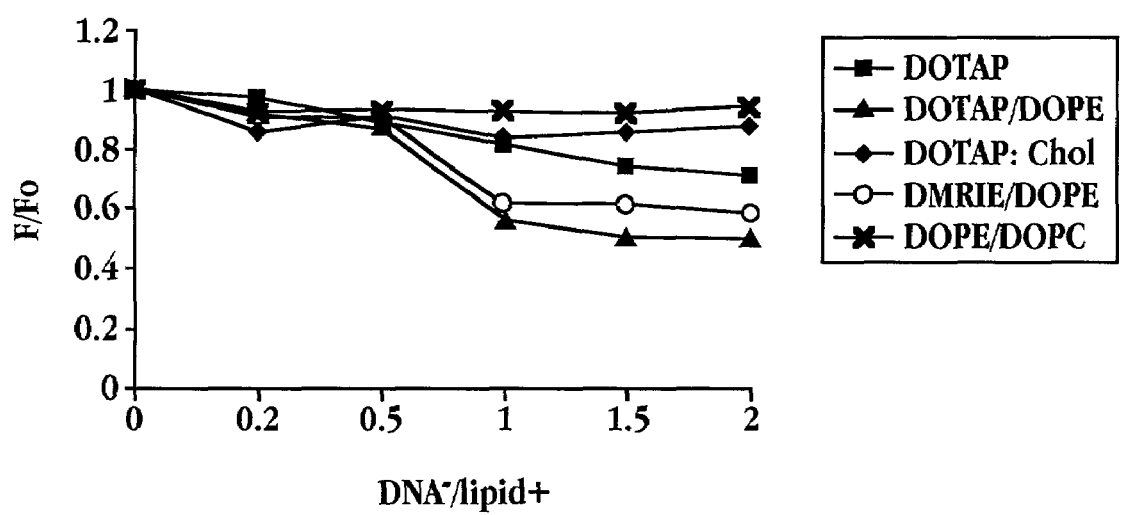
FIG. 9 shows the relative change in 528 nm fluorescence of aqueous preparations of LUV composed of DOTAP, DOTAP:DOPE, DOTAP:chol, DMRIE/DOPE, and DOPE/DOPC, respectively, each containing 0.2 mole % fluorescein-PE, on addition of increasing amounts of hGH-CMV DNA plasmid.
Figure 10:
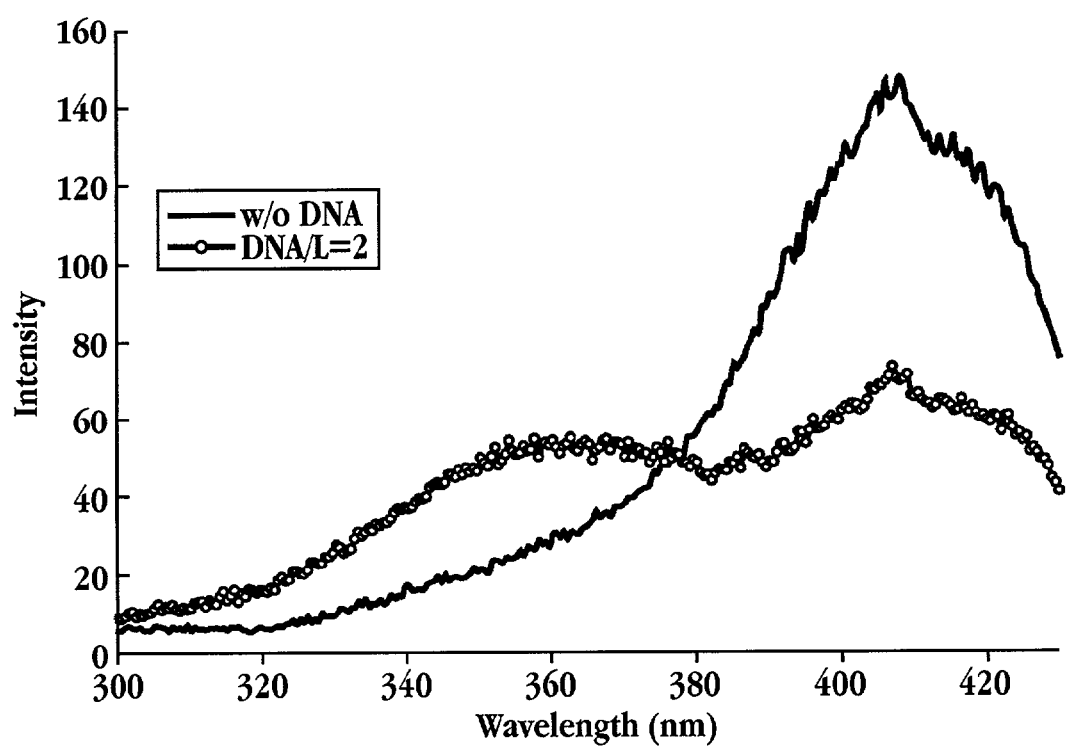
FIG. 10 shows the effect of adding DNA to DOTAP liposomes containing HC-PE probe, monitored through changes in the fluorescence emission intensity at 445 nm upon scanning of excitation wavelength.

FIG. 9 shows the relative change in 528 nm fluorescence of aqueous preparations of LUV composed of DOTAP, DOTAP/DOPE, DOTAP/chol, DMRIE/DOPE, and DOPE/DOPC, respectively, each containing 0.2 mole % fluorescein-PE, on addition of increasing amounts of hGH-CMV DNA plasmid. As can be seen, the change was greatest for the cationic liposomes. Similarly, FIG. 10 shows the effect of adding DNA to DOTAP liposomes, where the probe was HC-PE, monitored through changes in the fluorescence emission intensity at 445 nm.

Figure 11:
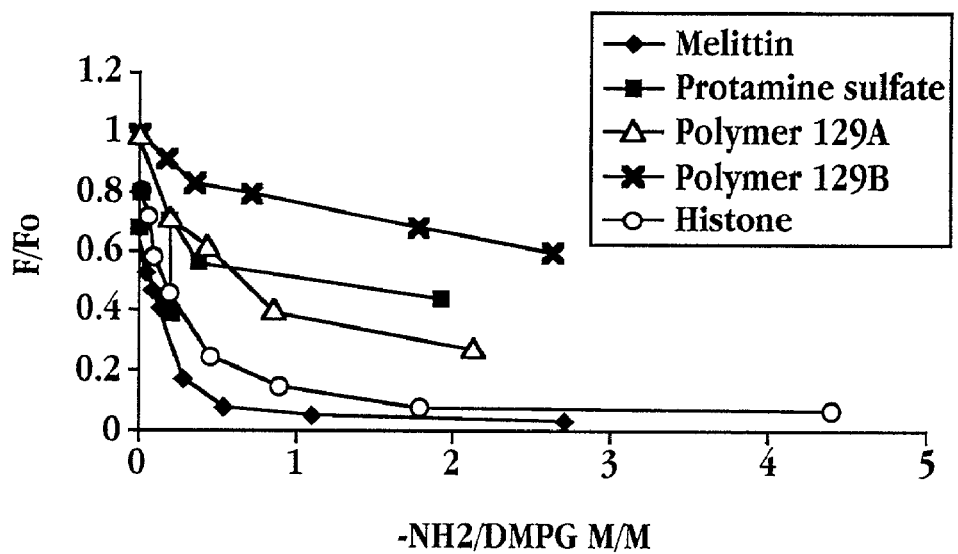
FIG. 11 shows the relative change in 585 nm fluorescence of aqueous preparations of anionic liposomes (MLV; 1:1 molar ratio DMPC/DMPG) containing 0.2 mole % pH-sensitive LR-PE, on addition of increasing amounts of various cationic polymers.

Binding of positively charged moieties to anionic surfaces may also be determined. As shown in FIG. 11, pH-sensitive LR-DOPE (0.2 mole %) was incorporated into DMPC/DMPG liposomes. Addition of various cationic proteins (melittin, protamine sulfate, and histone, respectively) had a strong effect on fluorescence, as shown in FIG. 11, while there was no evidence of binding to neutral or positively charged liposomes. The effect was also observed when a lower level of pH-sensitive LR-DOPE (0.2 mole %) was incorporated.

Figure 12A:
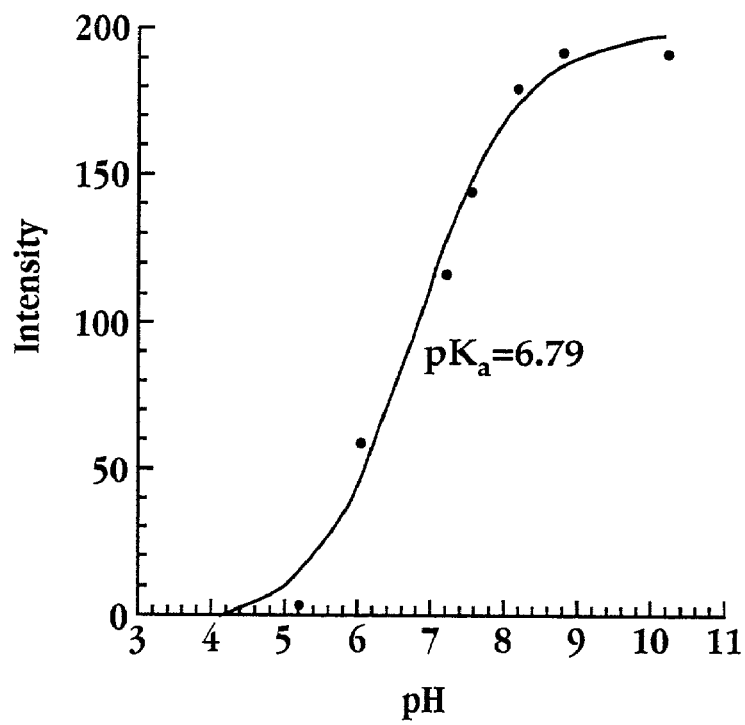
FIGS. 12A–B show the difference in pKa between a neutral polymer (dextran)-fluorescein conjugate and an oligonucleotide (AM-TIS)-fluorescein conjugate.
Figure 12B:
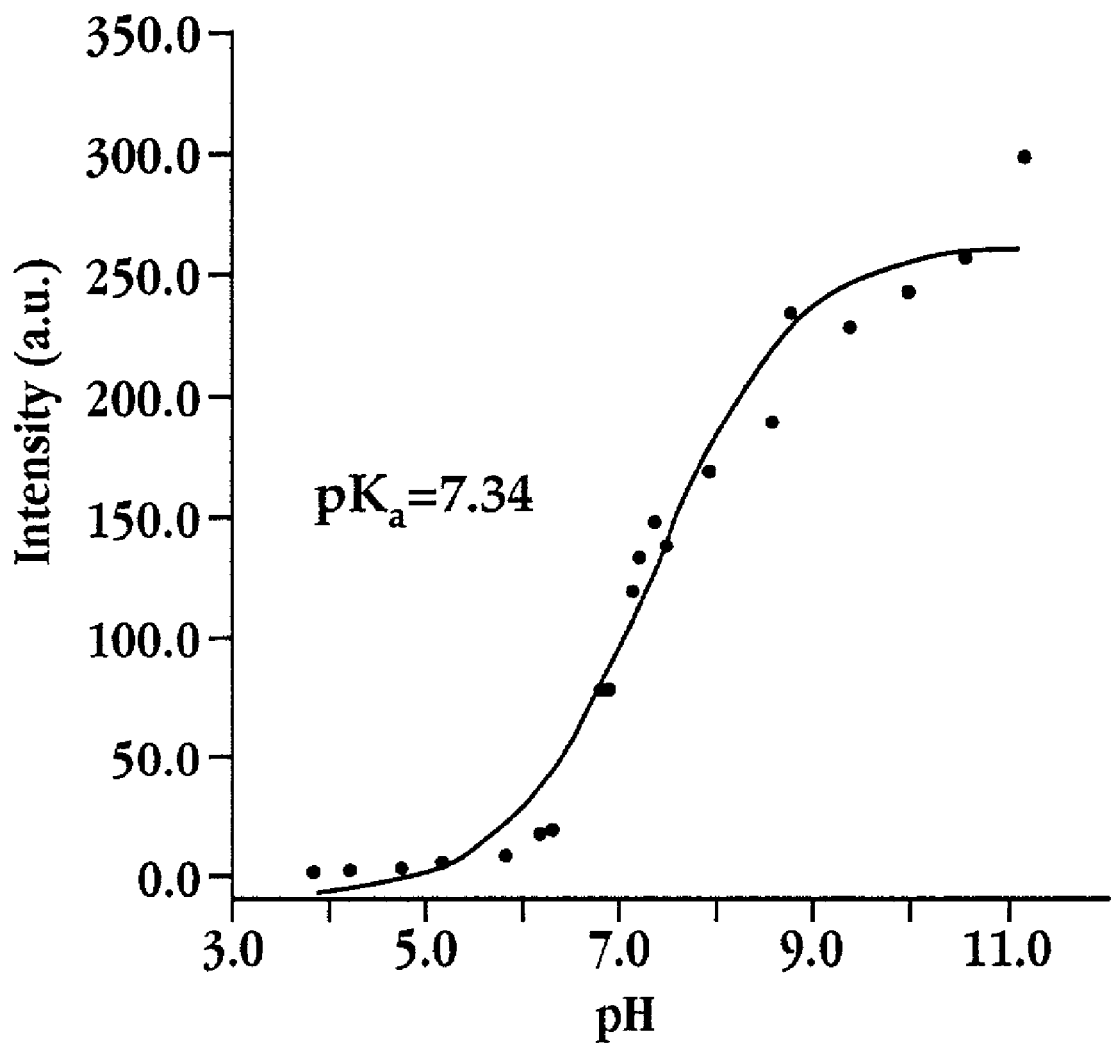
Figure 13:
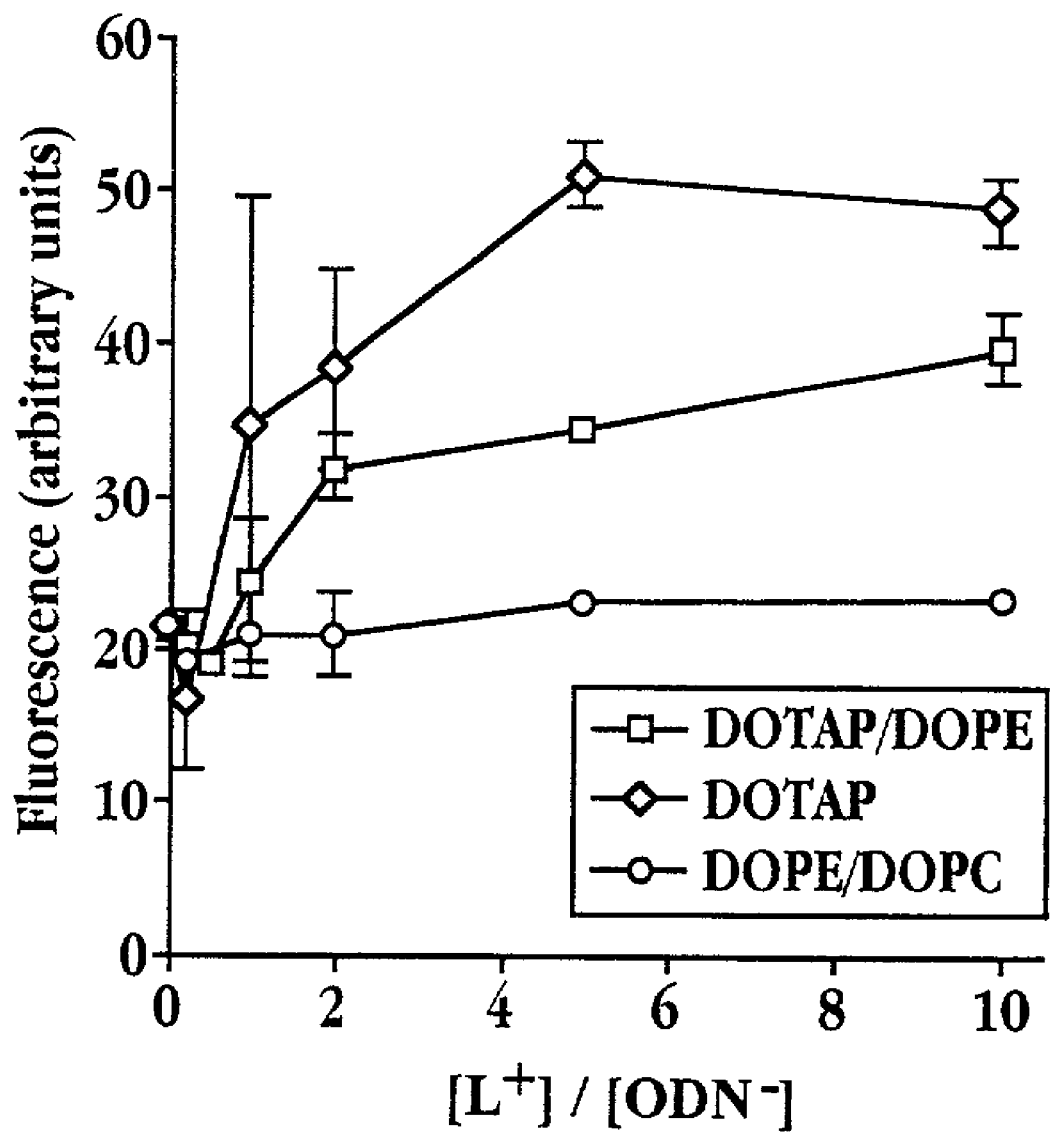
FIG. 13 shows the change in fluorescence of an FITC-labeled oligonucleotide (Bcl2-TIAS) on addition of increasing amounts of liposomes composed of DOTAP:DOPE, DOTAP, and DOPE/DOPC, respectively.

Binding to other surfaces can also be determined. For example, a cationic polymer, such as a polyamine, could be used as a binding surface for sequestering anionic species, such as nucleic acids, from solution. As shown in FIGS. 12A–12B, the pKa of the attached probe (in this case, fluorescein) is altered by the surface charge of the attached polymer or oligomer. FIG. 12A shows titration of a conjugate of fluorescein with a neutral polymer, dextran, where the conjugate has a pKa of about 6.8, while FIG. 12B shows titration of an oligonucleotide (AM-TIS)-fluorescein conjugate, having a pKa of about 7.3.

It will also be appreciated that dissociation of bound species from a surface will result in a reversal of the observed effect; e.g., for the experiments described above, dissociation of bound DNA from the DOTAP liposome would result in a decrease in fluorescence. Thus, transfection of DNA to cells via cationic liposomes may be monitored, in vitro or in vivo, using the present methods.

Figure 14:
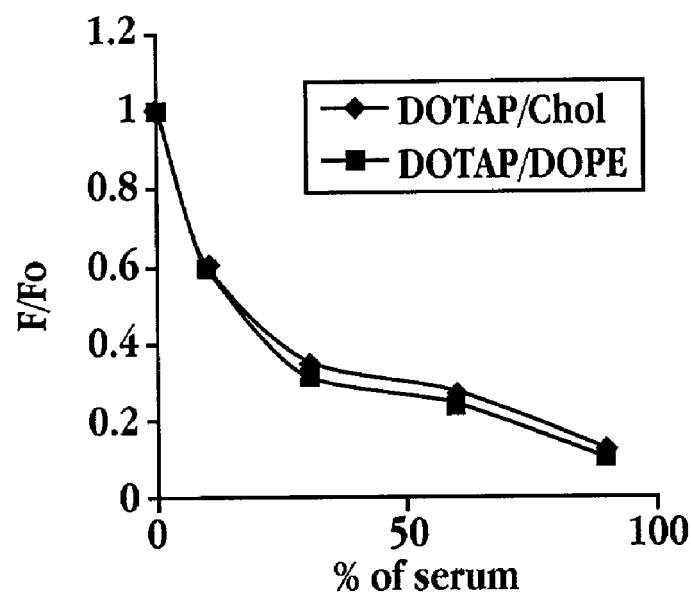
FIG. 14 shows the relative change in 528 nm fluorescence of aqueous preparations of MLV composed of DOTAP:DOPE and DOTAP:chol, respectively, each containing 0.2 mole % fluorescein-PE, on addition of increasing amounts of human blood serum.

FIG. 14 illustrates a variation on the method in which an oligonucleotide is labeled with a pH-dependent fluorophore, and the change in fluorescence, indicative of binding, is observed on addition of positively charged liposomes. FIG. 14 shows the change in fluorescence of an FITC-labeled oligonucleotide (Bcl2-TIAS) on addition of increasing amounts of liposomes composed of DOTAP:DOPE, DOTAP, and DOPE/DOPC, respectively. No change was observed with the neutral (zwitterionic) DOPE/DOPC liposomes.

E. Effect of Serum on Liposomes and Liposome-DNA Complexes (Lipoplexes)

Figure 15:
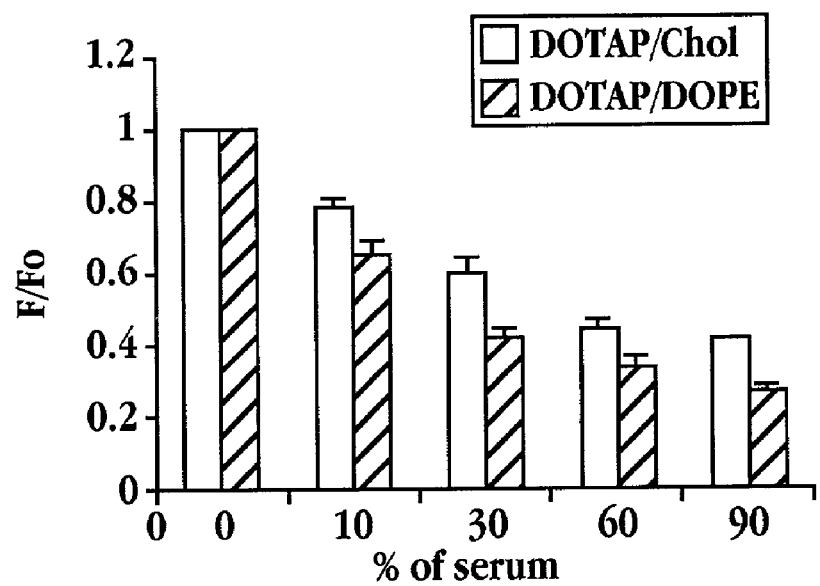
FIG. 15 shows the relative change in 528 nm fluorescence of aqueous preparations of DNA lipoplexes (DNA/lipid=0.5), where the liposomes are composed of DOTAP:DOPE and DOTAP:chol, respectively, each containing 0.2 mole % fluorescein-PE, on addition of increasing amounts of human blood serum.

The effect of adding human serum to DOTAP/chol and DOTAP/DOPE liposomes containing 0.2 mole % fluorescein-labeled DPPE is illustrated in FIG. 14. FIG. 15 shows the effect of adding human serum to liposome-DNA complexes (charge ratio DNA/lipid=0.5) prepared from DOTAP/chol and DOTAP/DOPE liposomes, containing 0.2 mole % fluorescein-labeled DPPE, and hGH-CMV DNA plasmid.

Studies in support of the invention showed that the interaction between plasma and DNA had a non-significant effect on fluorescence of the lipoplexes. The effects of each on fluorescence of the liposomal complexes were found to be roughly additive.

Addition of 5% plasma was compared with higher concentrations, up to 90% plasma, which is more representative of in vivo conditions. When 90% human plasma was added, the effect on fluorescence was substantial in both DOTAP/cholesterol and DOTAP/DOPE liposomes (containing F-PE probe), as shown in FIGS. 14–15. However, little effect was observed on (neutral) DOPC/DOPE liposomes (data not shown). The use of high plasma conditions provides an experimental method which approximates in vivo conditions, allowing prediction of in vivo liposome or lipoplex behavior.

EXAMPLES

The following examples illustrate but are not intended to limit the invention.

Example 1

Preparation of pH-sensitive Lissamine Rhodamine-Dioleoyl Phosphatidyl Ethanolamine (pH-sensitive LR-PE)

500 mg Dioleoyl phosphatidylethanolamine (DOPE) (500 mg) was placed into a 250 ml round bottom flask equipped with a magnetic stirrer and a dropping funnel. Isopropanol:dichloromethane (1:1 iPrOH:DCM) was added (100 ml), and the mixture was stirred until all the DOPE dissolved. Lissamine Rhodamine B chloride (LR-Cl, Molecular Probes L20, lot 1132-2; 380 mg) was added in one portion to the stirred solution. The mixture was stirred for 10 minutes, and 0.5 ml triethylamine (TEA) dissolved in 10 ml 1:1 iPrOH:DCM was added through the dropping funnel during a 60 minute period. The reaction was protected from light and stirred for 24 hours, after which time the solvent was removed. The dry residue was dissolved in 2 ml 1:1 iPrOH:DCM and applied to a preparative TLC plate, which was developed using 75:25:4 chloroform:MeOH:water. The desired isomer was isolated and further purified by preparative TLC, developing with 50:25:20:5 iPrOH:DCM:MeOH:ammonia.

Example 2

Preparation of 7-Hydroxycoumarin Dioleoyl Phosphatidyl Ethanolamine (HC-PE)

Dioleoyl phosphatidyl ethanolamine (DOPE) (4.8 mg) was dissolved in THF (2 ml); then 0.5 ml of pyridine was added, followed by 7-hydroxycoumarin-3-carboxylic acid succinimidyl ester (3.05 mg) dissolved in 2 ml THF. The solution was stirred overnight at room temperature under anhydrous conditions. The product was purified by preparative TLC on silica gel plates, developed with $CHCl_3$:MeOH:$H_2O$ in a ratio of 70:30:4.

Example 3

Preparation of Liposomes with Fluorescent Probe

Large unilamellar vesicles (LUV) were prepared by mixing tert-butyl alcohol solutions of the lipids with a fluorescently labeled lipid (e.g. F-PE, HC-PE or pH-sensitive LR-PE) in tert-butyl alcohol at a ratio of 1 mol of fluorophore per 400–500 mol of lipid. The mixture was freeze-dried overnight. The lyophilized cake was hydrated in 20 mM HEPES buffer (pH 7.4), and the suspension was vortexed to produce multilamellar vesicles (MLV). The MLV were extruded stepwise through 0.4 µm and then 0.1 µm polycarbonate filters (Poretics, Livermore, Calif.) mounted in the extruder Liposofast (Avestin, Ottawa).

Alternatively, MLV were prepared as follows, Mixtures of lipids in t-butanol solution with F-PE (total lipids:F-PE mole ratio (500:1)) were mixed in a 15-ml Falcon tube covered with an aluminum sheet, then lyophilized overnight to remove the solvent. The dried lipid cake was hydrated in 5% non-ionic glucose or 0.9% ionic NaCl by agitation on a vortex mixer for 5 minutes. Final total lipid concentration was about 31 mM.

Example 4

Preparation of ODN (Oligodeoxynucleotides) and Plasmid DNA he S-ODNs (AM-TIS: S-d-5'(GGG AAG GAT GGC GCA CGC TG), Bcl2-TIAS: S-d-5'(CAG CGT GCG CCA TCC TTC CC), AM-TIS-FITC: FITC-S-d-5'(GGG AAG GAT GGC GCA CGC TG) and Bcl2-TIAS-FITC: FITC-S-d-5' (CAG CGT GCG CCA TCC TTC CC)) were synthesized using the phosphoramidite method on an ABI 2-column synthesizer (Model #392). The sulfurization agent was 3H-1,2-benzodithol-3-one. The FITC-linked ODNs were prepared using 5'-FITC reagent. All ODNs were purified by precipitation twice from ethanol. Purified ODN was then dissolved in either a small volume of 20 mM HEPES buffer (pH 7.4) or 0.2 M acetate buffer (pH 5.7). If any precipitate was present, it was removed by centrifugation and isolation of the ODN-containing supernatant. The final ODN concentration was determined by conducting an organic phosphate assay.

Example 5

Preparation of Liposome-DNA Complexes and Determination of Plasma Effect

Lipoplexes were formed at room temperature in 3-ml single-use plastic cuvettes, which do not adsorb lipids, in place in a Perkin-Elmer spectrophotometer. Plasmid DNA diluted in HEPES/EDTA (20 mM pH 7.4 HEPES: 1 mM EDTA) was added to probe-containing liposomes (DOTAP or DOTAP combination), prepared as described in Example 3, to give a final volume of 3 ml. The lipid/DNA charge ratio varied from 2:1 (7.74 µl of 31 mM liposomes: 60 nmol DNA) to 1:2 (240 nmol DNA). Sample fluorescence was measured at 37° C. (wavelength dependent on probe), and the fluorescence intensity was followed until a plateau was reached. Each experiment was carried out in triplicate.

The invention claimed is:

1. A method for determining binding of a species at a lipid-based surface having a local environment at a given pH or surface potential, wherein said binding is effective to alter said pH or potential, the method comprising:

incorporating at said lipid-based surface a probe which comprises a pH- or potential-sensitive fluorophore attached to a steroid, to a head group of a sphingolipid or to a head group of a lipid having at least two chains, each chain comprising at least 14 carbon atoms in length, and wherein each independently said chain is selected from the group consisting of acyl, alkyl or alkenyl, wherein incorporation of the probe at the lipid-based surface is substantially not altered upon binding or dissociation of the species at the lipid-based surface and observing a change in a fluorescent property of said fluorophore retained at the surface upon binding or dissociation of said species at said lipid-based surface.

2. The method of claim 1, wherein said lipid-based surface is the surface of a lipid bilayer.

3. The method of claim 1, wherein said fluorophore is selected from the group consisting of a pH-sensitive lissamine rhodamine compound, 7-hydroxycoumarin, fluorescein, and pH- or potential-sensitive derivatives thereof.

4. The method of claim 1, wherein said lipid is a phospholipid.

5. The method of claim 3, wherein said phospholipid is a diacyl, dialkyl or dialkenyl phosphatidyl ethanolamine or ceramide phosphoethanolamine.

6. The method of claim 5, consisting of 7hydroxycoumarin conjugated via a 3-carboxamide linkage to the head group nitrogen of a diacyl, dialkyl, or dialkenyl phosphatidyl ethanolamine, or ceramide phosphoethanolamine.

7. The method of claim 1, wherein said species is a biomolecule having groups which are positively or negatively charged at a selected pH between about 2.0 and 12.0.

8. The method of claim 7, wherein said groups are positively or negatively charged at a selected pH between about 4.5 and 7.5.

9. The method of claim 7, wherein said biomolecule is a nucleic acid.

10. The method of claim 7, wherein said biomolecule is a protein comprising amino acids with acidic or basic side groups.

11. The method of claim 1, wherein said surface comprises groups which are positively or negatively charged at a selected pH between about 2.0 and 12.0.

12. The method of claim 11, wherein said groups are positively or negatively charged at a selected pH between about 4.5 and 7.5.

13. The method of claim 2, wherein said lipid bilayer comprises a lipid having a cationic head group.

14. The method of claim 1, wherein, upon said incorporating, said fluorophore is separated from said surface by a distance equal to or less than 15 nm.

15. The method of claim 1, wherein said lipid or steroid is attached to two or more fluorophores.

16. A method for detecting binding of a species to a given polymer surface having a defined pH or surface potential, said polymer surface being covalently attached to a probe which contains a pH- or potential-sensitive fluorophore, comprising:

a. contacting the species with the polymer surface covalently attached to the probe, wherein the species' binding to or dissociation of the species from the surface alters the pH or potential of the polymer surface; and b. observing change in an observable fluorescent property of the fluorophore, whereby a change of the observable property of the fluorophore indicates binding of the species to the polymer surface or dissociation of the species from the polymer surface.

17. The method of claim 16, wherein said fluorophore is covalently bound to said polymer.

18. A method for determining binding of a species at a surface having a local environment at a given pH or surface potential, wherein said binding is effective to alter said pH or potential, the method comprising:

stably incorporating at said surface a probe which comprises a pH- or potential-sensitive fluorophore attached to a steroid, to a head group of a sphingolipid or to a head group of a lipid having at least two hydrophobic chains, each said chain comprising at least 14 carbon atoms in length, and observing a change in a fluorescent property of said fluorophore upon binding or dissociation of said species at said surface.

19. The method according to claim 16 wherein the polymer is a cationic polysaccharide.

20. The method according to claim 19 wherein the cationic polysaccharide is dextran.

21. The method according to claim 16 wherein the fluorophore is selected from the group consisting of lissamine rhodamine, 7-hydroxycoumarin, fluorescein, and pH or potential-sensitive derivatives thereof.

* * * * *